United States Patent
Hoerger et al.

(10) Patent No.: US 8,382,836 B2
(45) Date of Patent: *Feb. 26, 2013

(54) METHOD TO IMPREGNATE A POROUS BONE REPLACEMENT MATERIAL

(75) Inventors: Flavio Hoerger, Zurich (CH); Thierry Stoll, Meinisberg (CH)

(73) Assignee: Synthes USA, LLC, West Chester, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/242,207

(22) Filed: Sep. 30, 2008

(65) Prior Publication Data
US 2009/0022878 A1   Jan. 22, 2009

Related U.S. Application Data

(63) Continuation of application No. 11/349,693, filed on Feb. 7, 2006, now Pat. No. 7,445,633, which is a continuation of application No. PCT/CH03/00537, filed on Aug. 8, 2003.

(51) Int. Cl.
*A61F 2/28* (2006.01)
(52) U.S. Cl. .................................. 623/16.11
(58) Field of Classification Search ............. 623/16.11; 366/139
See application file for complete search history.

(56) References Cited

U.S. PATENT DOCUMENTS

| | | | |
|---|---|---|---|
| 4,314,380 A * | 2/1982 | Miyata et al. | 623/23.61 |
| 4,529,511 A | 7/1985 | Breeden et al. | |
| 4,758,096 A | 7/1988 | Gunnarsson | |
| 4,808,184 A | 2/1989 | Tepic | |
| 5,051,482 A | 9/1991 | Tepic | |
| 5,139,031 A | 8/1992 | Guirguis | |
| 5,164,186 A | 11/1992 | Tsuru et al. | |
| 5,181,918 A | 1/1993 | Brandhorst et al. | |
| 5,425,770 A | 6/1995 | Piez et al. | |
| 5,549,380 A | 8/1996 | Lidgren et al. | |
| 5,755,787 A | 5/1998 | Camprasse et al. | |
| 5,772,665 A | 6/1998 | Glad et al. | |

(Continued)

FOREIGN PATENT DOCUMENTS

| | | |
|---|---|---|
| CA | 2419850AA | 2/2002 |
| DE | 3834944 | 4/1990 |

(Continued)

OTHER PUBLICATIONS

"International Application Serial No. PCT/CH03/00537, International Search Report mailed Apr. 16, 2004", 3 pgs.

(Continued)

*Primary Examiner* — Tony G Soohoo
(74) *Attorney, Agent, or Firm* — Woodcock Washburn LLP

(57) ABSTRACT

A method to impregnate a porous bone replacement material (1) with a liquid impregnating agent (5), wherein
a) the bone replacement material (1) is or will be enclosed in a chamber (2) with two openings (3, 4) that can be closed,
b) the impregnating agent (5) is introduced into the chamber (2) until the bone replacement material (1) is at least partly immersed in the impregnating agent (5),
c) one of the two openings (3, 4) will be closed,
d) the chamber (2) is evacuated at least partly via the other, open, opening (4, 3), so that the air contained in the pores of the bone replacement material (1) is at least partly removed from it,
e) the vacuum produced in the chamber is terminated again by supplying air or a gas through one of the openings (3, 4), and
f) the vacuum produced in the pores of the bone replacement material (1) is terminated by the impregnating agent (5) penetrating into the pores of the bone replacement material (1) immersed into the impregnating agent (5).

16 Claims, 2 Drawing Sheets

U.S. PATENT DOCUMENTS

| | | | |
|---|---|---|---|
| 5,842,786 | A | 12/1998 | Solomon |
| 5,876,452 | A | 3/1999 | Athanasiou et al. |
| 6,027,742 | A | 2/2000 | Lee et al. |
| 6,049,026 | A | 4/2000 | Muschler |
| 6,143,293 | A * | 11/2000 | Weiss et al. ............ 424/93.7 |
| 6,383,190 | B1 | 5/2002 | Preissman |
| 6,409,708 | B1 | 6/2002 | Wessman |
| 6,709,149 | B1 | 3/2004 | Tepic |
| 6,723,131 | B2 * | 4/2004 | Muschler ............. 623/23.51 |
| 6,736,799 | B1 | 5/2004 | Erbe et al. |
| 6,887,272 | B2 | 5/2005 | Shinomiya et al. |
| 7,445,633 | B2 * | 11/2008 | Hoerger et al. ........ 623/16.11 |
| 2002/0161449 | A1 * | 10/2002 | Muschler ............. 623/23.51 |
| 2005/0074433 | A1 | 4/2005 | Stoll |
| 2006/0153001 | A1 | 7/2006 | Hoerger et al. |

FOREIGN PATENT DOCUMENTS

| | | | |
|---|---|---|---|
| EP | 0361896 | A2 | 4/1990 |
| EP | 0470393 | A1 | 2/1992 |
| EP | 0739631 | A2 | 10/1996 |
| EP | 0761896 | A1 | 3/1997 |
| EP | 1230942 | A2 | 8/2002 |
| FR | 2815021 | A1 | 4/2002 |
| JP | 60-142857 | | 7/1985 |
| JP | 3-85179 | | 4/1991 |
| JP | 4-221538 | | 8/1992 |
| JP | 7-313586 | | 12/1995 |
| JP | 8-24347 | | 1/1996 |
| JP | 9-201330 | | 8/1997 |
| WO | WO-9746202 | A1 | 12/1997 |
| WO | WO-00/45867 | A1 | 8/2000 |
| WO | WO-01/32100 | A2 | 5/2001 |
| WO | WO 02/15950 | * | 2/2002 |
| WO | WO-02/15950 | A1 | 2/2002 |
| WO | WO-02/068010 | A1 | 9/2002 |
| WO | WO 2005/014068 | * | 2/2005 |
| WO | WO-2005/014068 | A1 | 2/2005 |

OTHER PUBLICATIONS

"Definition of Osteogenic", [online]. © 2005 Merriam-Webster, Inc. [retrieved May 16, 2005]. Retrieved from the Internet: <URL: www.nlm.nih.gov/medlineplus/mplusdictionary.html>, 1 pg.

"Definition of Body", *Random House Webster's College Dictionary*, (1991), p. 152.

Linkhart, T. A ., et al., "Growth factors for bone growth and repair: IGF, TGFβ and BMP", *Bone, 19(1 Suppl)*, (Jul. 1996), 1S-12S.

"U.S. Appl. No. 10/370,606 Advisory Action mailed Aug. 11, 2008", 4 pgs.

"U.S. Appl. No. 10/370,606, Non-Final Office Action mailed Oct. 31, 2008", 17 pgs.

"U.S. Appl. No. 10/370,606, filed Mar. 16, 2007 to Non-Final Office Action mailed Dec. 18, 2006", 6 pgs.

"U.S. Appl. No. 10/370,606, filed Mar. 20, 2006 to Non-Final Office Action mailed Dec. 19, 2005", 23 pgs.

"U.S. Appl. No. 10/370,606, filed Jul. 31, 2006 to Final Office Action mailed May 31, 2006", 10 pgs.

"U.S. Appl. No. 10/370,606, filed Jun. 26, 2008 to Final Office Action mailed May 1, 2008", 11 pgs.

"U.S. Appl. No. 10/370,606, filed Aug. 22, 2008 to Advisory Action mailed Aug. 11, 2008", 11 pgs.

"U.S. Appl. No. 10/370,606, filed Sep. 17, 2007 to Final Office Action mailed Jun. 15, 2007", 10 pgs.

"U.S. Appl. No. 10/370,606, Non-Final Office Action mailed Dec. 11, 2007", 14 pgs.

"U.S. Appl. No. 10/370,606, Final Office Action mailed May 1, 2008", 14 pgs.

"U.S. Appl. No. 10/370,606, Response to Non-Final Office Action received Dec. 11, 2007", 10 pgs.

"U.S. Appl. No. 10/370,606, Final Office Action mailed May 31, 2006", 15 pgs.

"U.S. Appl. No. 10/370,606, Final Office Action mailed Jun. 15, 2007", 10 pgs.

"U.S. Appl. No. 10/370,606, Non Final Office Action mailed Dec. 18, 2006", 6 pgs.

"U.S. Appl. No. 10/370,606, Non Final Office Action mailed Dec. 19, 2005", 14 pgs.

"U.S. Appl. No. 11/349,693, Non-Final Office Action mailed Sep. 7, 2007", 9 pgs.

"U.S. Appl. No. 11/349,693, filed Jun. 16, 2008 to Final Office Action mailed Mar. 17, 2008", 8 pgs.

"U.S. Appl. No. 11/349,693, filed Dec. 7, 2007 to Office Action mailed Sep. 7, 2007", 10 pgs.

"U.S. Appl. No. 11/349,693, Notice of Allowance mailed Jun. 30, 2008", 7 pgs.

"U.S. Appl. No. 11/349,693, Final Office Action mailed Mar. 17, 2008", 10 pgs.

"Definition of "Membrane"", *The American Heritage Dictionary of the English Language*, [online]. Answers.com™. [retrieved Jul. 31, 2008]. Retrieved from the Internet: <URL: http://www.answers.com/membrane%26r=67?print=true>, (2007), 2 pgs.

Definition of "mesenchymal", Dictionary.com, [online]. *Merriam-Webster's Medical Dictionary*, © 2002 Merriam-Webster. [retrieved on Dec. 13, 2005]. Retrieved from the Internet:: <URL: http://dictionary.reference.com/search?q=mesenchymal>, 1 pg.

"Definition of "Osteogenic"", *Medline Plus®*, [online]. © 2005 Merriam-Webster, Incorporated. [retrieved Dec. 12, 2005]. Retrieved from the Internet: <URL: http://ww2.merriam-webster.com/cgi-bin/mwmednlm?book=Medical&va?osteogenic>, 1 pg.

Definitions of "vaccum", "membrane", and "septum", *MedLine Plus®*, [online].[retrieved Oct. 16, 2008]. Retrieved from the Internet: <URL: http://www.nim.nih.gov/medlineplus/mplusdictionary.html>, 3 pgs.

"EPOline Online Public File Inspection entry for International Application No. WO2000CH00443", [online]. [retrieved Dec. 13, 2005]. Retrieved from the Internet: <URL: http://ofi.epoline.org/view/GetDossier>, 1 pg.

"European Patent Application No. 04750971.6, Communication mailed Jun. 12, 2008", 5 pgs.

"International Application Serial No. PCT/CH01/00494, International Preliminary Examination Report dated Aug. 26, 2002", (w/ English Translation),15 pgs.

"International Application Serial No. PCT/CH01/00494, International Search Report mailed Dec. 5, 2001", (w/ English Translation), 8 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling of poly(N-isopropylacrylamide) hydrogels grafted with LCST modulated polymers", *Journal Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

"U.S. Appl. No. 10/370,606, Final Office Action mailed May 21, 2009", 16 pgs.

"U.S. Appl. No. 10/370,606, filed Sep. 21, 2009 to Final Office Action mailed May 21, 2009", 9 pgs.

"U.S. Appl. No. 10/370,606, filed Feb. 26, 2009 to Non Final Office Action mailed Oct. 31, 2008", 9 pgs.

"Canada Application Serial No. 2,419,850, Office Action mailed Jul. 7, 2009", 3 pgs.

* cited by examiner

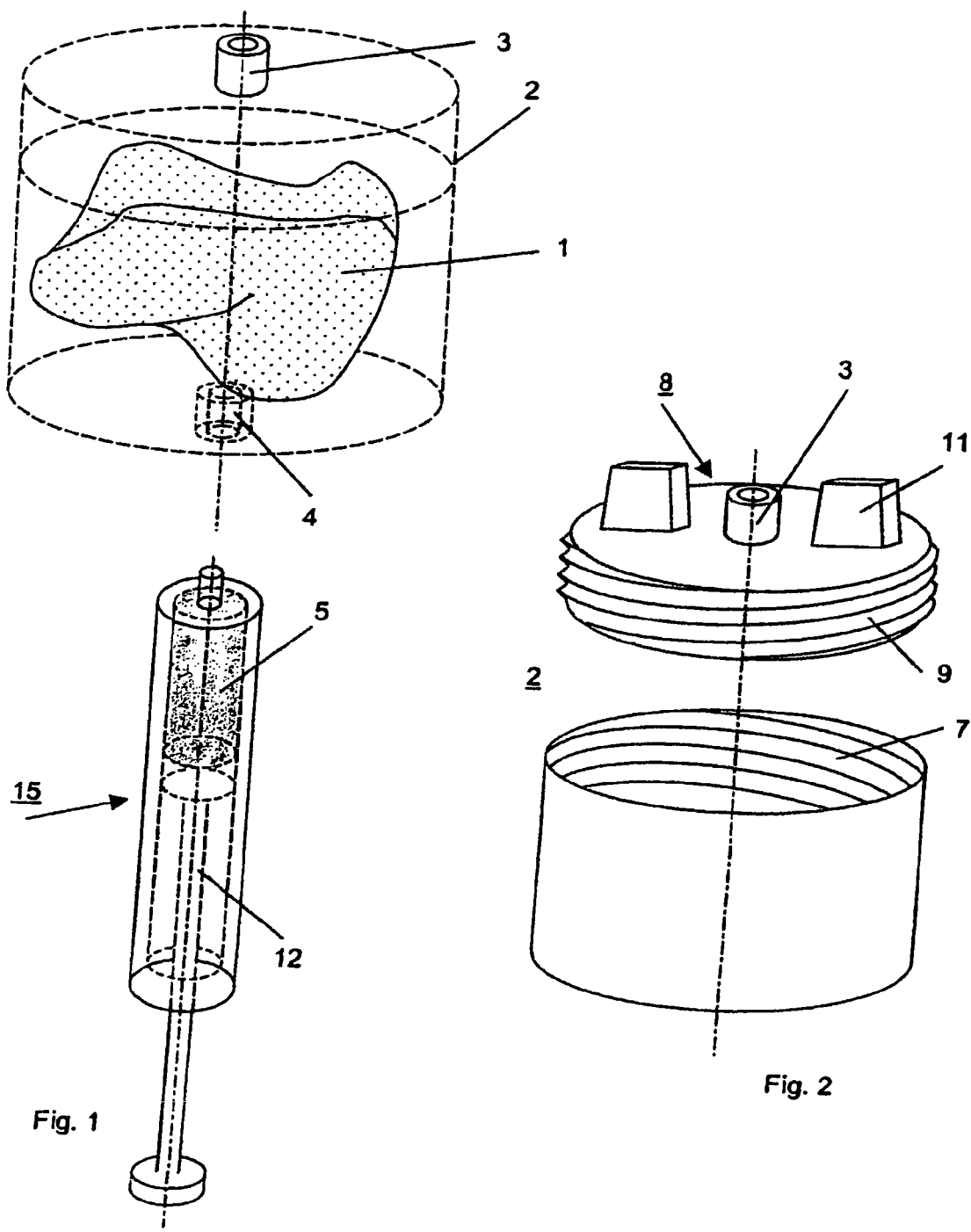

METHOD TO IMPREGNATE A POROUS BONE REPLACEMENT MATERIAL

RELATED APPLICATIONS

This application is a continuation of U.S. patent application Ser. No. 11/349,693, filed on Feb. 7, 2006, now U.S. Pat. No. 7,445,633, which is a continuation application of International Patent Application Serial No. PCT/CH2003/000537, filed Aug. 8, 2003, the contents of which are incorporated herein by reference in their entirety.

INTRODUCTION

The invention concerns a method to impregnate a porous bone replacement material, as well as a chamber to impregnate a porous bone replacement material.

BACKGROUND OF THE INVENTION

From WO 02/068010 Muschler a device is known, in which a bone marrow extract is mechanically mixed with a porous bone replacement material. In this conjunction the bone marrow extract can be squeezed into or aspirated through the bone replacement material by means of two syringes, so that it will be flushed by the bone marrow extract. Consequently, in the case of this known method the air situated in the bone replacement material will not be removed.

A further device to impregnate a porous, biocompatible bone replacement substance is known from U.S. Pat. No. 6,049,026 Muschler. This known device comprises a chamber to accommodate the bone replacement body as well as a first container above the chamber to store an impregnating agent and below the chamber a second container to accommodate the impregnating agent flowing through the chamber with the bone replacement substance in it. By opening the first valve, arranged between the first container and the chamber, the impregnating agent flows into the chamber with the bone replacement substance. As soon as the chamber is filled, a second valve, arranged between the chamber and the second container, is opened, so that the impregnating agent can flow to the second chamber through a diaphragm provided below the bone replacement substance. A disadvantage of this known device is that the capacity of the chamber cannot be modified, so that for bone replacement bodies of various sizes chambers of varying sizes are required.

In the case of the usually applied method, whereby such formed bodies from porous bone replacement materials are placed into a shell with the patient's own blood, these known devices also have the disadvantages that during the impregnation it is not assured that solid blood constituents, like for example blood platelets or other cells would be able to advance up to the core of the implant. The blood cells will concentrate and hold firmly at the edges of the implant (filtering effect of the bone replacement material), and the entire air could be removed from the implant. Air inclusions form a barrier for the growing in of the bone and hinder the transformation of the resorbable bone replacement material.

SUMMARY OF THE INVENTION

This is where the invention wants to provide remedy. The object of the invention is to produce a method to impregnate a porous bone replacement material that removes the air situated in the pores of the bone replacement material and replaces it with the desired impregnating agent.

This invention achieves this objective by a method to impregnate a porous bone replacement material, as well as by a chamber for the impregnation of a porous bone replacement material.

In certain embodiments of the invention, the method comprises impregnating a porous bone replacement material with a liquid impregnating agent, characterised in that a) the bone replacement material is or will be enclosed in a chamber with two openings that can be closed, b) impregnating agent is introduced into the chamber until the bone replacement material is at least partly immersed in the impregnating agent, c) one of the two openings will be closed, d) the chamber is evacuated at least partly via the other, open, opening so that the air contained in the pores of the bone replacement material is at least partly removed from it, and e) the vacuum produced in the chamber is terminated again by supplying air or a gas through one of the openings so that f) the vacuum produced in the pores of the bone replacement material is terminated by the impregnating agent penetrating into the pores of the bone replacement material immersed into the impregnating agent.

In certain embodiments of the invention, the chamber comprises a cylindrical container with a hollow space, an internal thread provided in the hollow space and a matching lid with external thread and that the internal capacity V of the chamber is variable by screwing the lid into the cylindrical container to a greater or lesser depth.

Further advantageous configurations of the invention are characterised in the dependent claims.

The advantages achieved by the invention are essentially that as a result of the method according to the invention the air, situated in the pores of the bone replacement material, can be removed and the desired impregnating agent can penetrate into the pores.

In a preferred embodiment the air or gas is evacuated upwards through the opening provided in the chamber against the gravity vector, so that the impregnating agent will be retained in the chamber by the gravity.

The bone replacement material can be present in the form of a block, preferably in the form of a dice, cylinder, hollow cylinder, disc, wedge, cone, truncated cone or a sphere or in another execution of the method in the form of granules.

In yet another execution the impregnating agent comprises osteoinductive and/or osteogenic substances, in particular body cells, bone marrow or bone marrow components, blood or blood constituents or a combination thereof.

In a further execution, by means of the vacuum, produced in step d) of the method, the ambient pressure initially prevailing in the chamber is reduced from 1 bar to below 0.9 bar, preferably below 0.6 bar.

In yet another further execution of the method by means of the vacuum, produced in step d) of the method, the ambient pressure initially prevailing in the chamber is reduced from 1 bar to below 0.2 bar, preferably below 0.1 bar.

The introduction of the impregnating agent can be carried out by aspirating the impregnating agent through one of the two openings of the chamber by the flow-through of the negative pressure, by pressing in the impregnating agent through one of the two openings of the chamber by the flow-through of the excess pressure, or by multiple repeating of the steps d) and e) of the method.

In a preferred embodiment the internal capacity V of the chamber is variable, whereby the chamber preferably comprises a cylindrical container with an internal thread and a matching lid with external thread, so that the internal capacity V of the chamber is variable by screwing the lid into the cylindrical container to a greater or lesser depth. This will result in the advantage, that a single size chamber will be adequate to accommodate implants of various sizes.

Because the chamber will be filled in this manner with a porous bone replacement material, the total capacity v of which is smaller than the internal volume V of the chamber, the bone replacement material can be partly or fully immersed in the impregnating agent.

In another execution of the chamber the bone replacement material is accommodated in an implant made from metal and/or plastic material in such a manner, that it communicates, at least partly, with the surface of the implant.

The invention and developments of the invention are explained in detail below, based on partly schematic illustrations of a plurality of embodiments.

BRIEF DESCRIPTION OF THE DRAWINGS

FIG. 1—a perspective view of a chamber to carry out the method according to the invention, together with a syringe, FIG. 2—an exploded view of a chamber to carry out the method according to the invention, FIG. 3—a longitudinal section through a chamber to carry out the method according to the invention, FIG. 4—a top view on the chamber illustrated in FIG. 3 to carry out the method according to the invention.

DETAILED DESCRIPTION OF THE INVENTION

Figure 3:
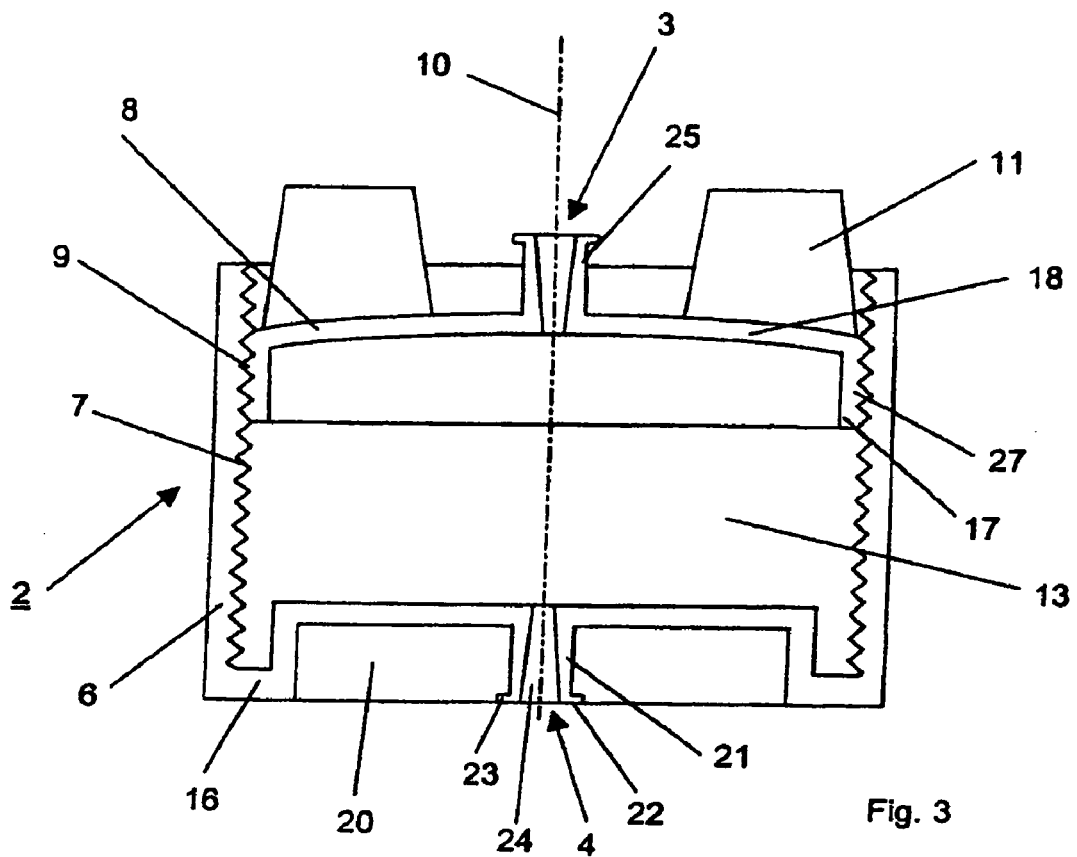

The present invention relates a method to impregnate a porous bone replacement material with a liquid impregnating agent, characterised in that
  a) the bone replacement material is or will be enclosed in a chamber with two openings that can be closed,
  b) the impregnating agent is introduced into the chamber until the bone replacement material is at least partly immersed in the impregnating agent,
  c) one of the two openings will be closed,
  d) the chamber is evacuated at least partly via the other, open, opening, so that the air contained in the pores of the bone replacement material is at least partly removed from it, and
  e) the vacuum produced in the chamber is terminated again by supplying air or a gas through one of the openings, so that
  f) the vacuum produced in the pores of the bone replacement material is terminated by the impregnating agent penetrating into the pores of the bone replacement material immersed into the impregnating agent.

In certain embodiments, the method is characterised in that in the step d) the air or the gas is evacuated through the opening provided on the top of the chamber against the gravity vector.

In certain embodiments, the method is characterised in that the bone replacement material is present in the form of a block, preferably in the form of a dice, cylinder, hollow cylinder, disc, wedge, cone, truncated cone or a sphere.

In certain embodiments, the method is characterised in that the bone replacement material is present in the form of granules.

In certain embodiments, the method is characterised in that the impregnating agent comprises osteoinductive and/or osteogenic substances, in particular body cells, bone marrow or bone marrow components, blood or blood constituents or a combination thereof.

In certain embodiments, the method is characterised in that the vacuum, produced in step d), reduces the pressure initially prevailing in the chamber from 1 bar to below 0.9 bar, preferably below 0.6 bar.

In certain embodiments, the method is characterised in that the vacuum, produced in step d), reduces the pressure initially prevailing in the chamber from 1 bar to below 0.2 bar, preferably below 0.1 bar.

In certain embodiments, the method is characterised in that the impregnating agent is introduced into the chamber by aspiration through one of the two openings by the flow-through of the negative pressure.

In certain embodiments, the method is characterised in that the impregnating agent is introduced into the chamber by pressing it through one of the two openings by the flow-through of the excess pressure.

In certain embodiments, the method is characterised in that steps d) and e) of the method are repeated several times.

The present invention also relates to a chamber to impregnate a porous bone replacement material with an impregnating agent, wherein the chamber has two openings that can be closed and an internal capacity V, characterised in that the internal volume V of the chamber can be varied.

In certain embodiments, the chamber is characterised in that it comprises a cylindrical container with a hollow space, an internal thread provided in the hollow space and a matching lid with external thread and that the internal capacity V of the chamber is variable by screwing the lid into the cylindrical container to a greater or lesser depth.

In certain embodiments, the chamber is characterised in that the chamber contains a porous bone replacement material, the total capacity v of which is smaller than the internal volume of the chamber.

In certain embodiments, the chamber is characterised in that the bone replacement material is present in the form of a block, preferably in the form of a dice, cylinder, hollow cylinder, disc, wedge, cone, truncated cone or a sphere.

In certain embodiments, the chamber is characterised in that the bone replacement material is accommodated in an implant made from metal and/or plastic material in such a manner, that it communicates, at least partly, with the surface of the implant.

FIG. 1 shows a chamber 2 with a body, consisting of the bone replacement material 1 and enclosed in the hollow space. The chamber 2 has two openings 3, 4, that can be connected airtight with a syringe 15. As impregnating agent 5 the syringe 15 may contain in its hollow chamber osteoinductive and/or osteogenic substances, in particular body cells, bone marrow and/or bone marrow components, blood and/or blood constituents. Together with the syringe 15, the chamber 2 illustrated here serves the purpose of carrying out the method according to the invention, comprising the following steps:
  a) a syringe 15, filled with the impregnating agent 5, is preferably connected to the bottom opening 4 of the chamber 2. The top opening 3 remains open. Both openings 3, 4 are constructed as Luer-openings with a connecting piece 21, 25 each, joined with the chamber 2 and having tapered bores. The impregnating agent 5 is now injected by means of the piston 12 through the bottom opening 4 into the chamber 2, so that the block of porous bone replacement material 1 is surrounded by the impregnating agent 5 and is immersed therein partially or completely;

b) the top opening 3 is now closed off;

c) following this the piston 12 of the syringe 5 is withdrawn, so that a negative pressure or vacuum will occur in the chamber 2. By virtue of the vacuum the air existing in the pores of the bone replacement material 1 expands, so that it exits from the pores into the surrounding impregnating agent 5. Since one deals here with a closed system, the impregnating agent 5 is aspirated only partly by the movement of the piston. This is also feasible only when air is still contained in the chamber 2. A large number of impregnating agents 5 may have adhesive properties, so that they adhere to the surface of the bone replacement material 1 and will not be aspirated by the movement of the piston;

d) in the next step the piston 12 of the syringe 5 is pressed in the original position, so that the vacuum in the chamber 2 will be terminated. The block of bone replacement material 1, surrounded by the impregnating agent 5 does not, of course, now absorb air in its pores but impregnating agent 5, so that an impregnation of the bone replacement material 1 takes place. The evacuation/cancellation of the vacuum in the chamber 2, that can be carried out by means of the syringe 5, can be repeated several times to increase the degree of impregnation. By virtue of its adhesion and the capillary effect of the structure of the porous bone replacement material 1 the impregnating agent 5 will be more likely be absorbed than air.

Another execution of the method is such, that after the first syringe 15, filled with the impregnating agent 5, is connected to one of the two openings 3, 4, a second, unfilled syringe 15 (not illustrated) is connected to the other opening 3, 4, and the hollow space of the chamber 2 is evacuated by withdrawing the piston and simultaneously, due to the negative pressure produced, the impregnating means 5 is aspirated from the hollow space of the syringe 15 into the hollow space of the chamber 2. The air in the pores of the bone replacement material 1 exits from the pores. Following this, by pushing in the piston of the second syringe, air is moved again into the chamber 2, so that the vacuum is terminated again in the chamber 2 and the impregnating agent 5 can penetrate into the pores of the bone replacement material. If necessary, the piston of one of the syringes can be withdrawn and the chamber 2 can be evacuated again. The steps of evacuation and cancellation of the vacuum can be simply repeated in this manner until the pores in the bone replacement material 1 are adequately ventilated and filled with the impregnating material 5.

According to yet another execution of the method the second syringe (not illustrated) is used to increase the vacuum. Because this second syringe is not filled with impregnating agent 5, it can have a considerably greater capacity than the first syringe 15, filled with impregnating agent 5.

Figure 4:
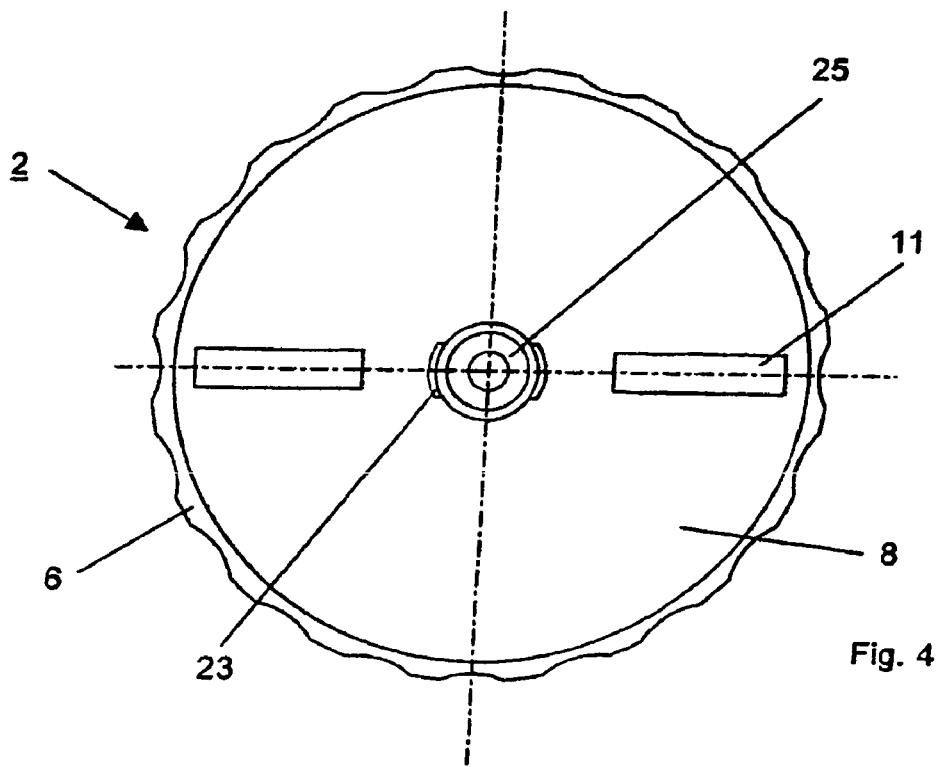

FIGS. 2-4 illustrate an embodiment of the chamber 2, that comprises a cylindrical container 6 coaxial with the central axis 10 and a coaxially fastenable lid 8. In its hollow space 13 the container 6 has an internal thread 7 that is coaxial with the central axis 10, so that the lid 8, having on its jacket surface an external thread 9 that matches the internal thread 7, can be detachably joined with the container 6. The internal thread 7 in the container 6 extends over the entire length of the hollow space 13. The external thread 9 on the lateral jacket surface of the lid 8 extends over the entire axial length of the lid 8, so that the lid 8 can be screwed also into the hollow space 13 of the container 6 and consequently the free capacity in the hollow space 13 of the container 6 can be reduced until the front end 17 of the tubular extension 27 of the lid 8 abuts against the bottom 16 of the container 6. The internal thread 7, as well as the external thread 9, are executed as multi-start threads. The bottom 16 of the container 6 has a depression 20, where a connecting piece 21 with a central bore 24 and concentric with the central axis 10, is provided. The central bore 24 of the connecting piece 21 forms the opening 4. At its free end 22 the connecting piece 21 is provided with two radially protruding cams 23, so that a standard syringe 15, having a construction matching the connecting piece 21 and an internal thread on its opening, can be screwed over the connecting piece 21 (Luer joint). Instead of the Luer-joint the central bores 24 of the connecting pieces 21, 25 can have a tapered shape in such a manner, that a syringe 15 with standard taper can be introduced into one of the central bores 24 of the connecting pieces 21, 25 and fastened by means of the tapered connection. The connections can be chosen also in such manner, that various adapters can be joined in an airtight manner. By virtue of arranging the connecting piece 21 in the depression 20 in such a manner, that the connecting piece 21 does not protrude past the bottom 16 of the container 6, the container 6 can be placed on its bottom without tipping. Similarly to that on the outside of the cover plate 18 of the lid 8 a second connecting piece 25 is provided, that is bored through concentrically with the central axis 10. The connecting pieces 21, 25 are identical. To facilitate the screwing on or off the chamber 2, two axially protruding protrusions 11 are provided on the outside of the cover plate 18 of the lid 8 and axially extending grooves 26 on the outer jacket surface of the container 6.

While the foregoing description and drawings are merely illustrative of the principles of the invention, it will be understood that various additions, modifications and substitutions may be made therein. In particular, it will be clear to those skilled in the art that the present invention may be embodied in other specific forms, structures, arrangements, proportions, and with other elements, materials, and components, without departing from the spirit or essential characteristics thereof. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed:

1. A method for impregnating a porous bone replacement material, comprising:

enclosing a porous bone replacement material in a chamber with two openings that can be closed;

introducing a liquid impregnating agent into the chamber until the porous bone replacement material is at least partly immersed in the liquid impregnating agent;

closing one of the two openings of the chamber;

evacuating the chamber at least partly through the other opening so that the air contained in the pores of the porous bone replacement material is at least partly removed from it; and terminating the vacuum produced in the chamber by supplying air or a gas through one of the two openings of the chamber so that the vacuum produced in the pores of the porous bone replacement material is terminated by the impregnating agent penetrating into the pores of the porous bone replacement material immersed into the liquid impregnating agent.

2. The method according to claim 1, wherein the air is removed through the opening provided on the top of the chamber against the gravity vector.

3. The method according to claim 1, wherein the material is in the form of a dice, cylinder, hollow cylinder, disc, wedge, cone, truncated cone or a sphere.

4. The method according to claim 1, wherein the liquid impregnating agent comprises one or more osteoinductive and/or osteogenic substances.

5. The method according to claim 4, wherein the one or more osteoinductive and/or osteogenic substances is a body cell, bone marrow or bone marrow component, blood or blood constituent, or a combination thereof.

6. The method according to claim 1, wherein the vacuum reduces a pressure initially prevailing in the chamber from 1 bar to below 0.9 bar.

7. The method according to claim 6, wherein the vacuum reduces the pressure initially prevailing in the chamber to below 0.6 bar.

8. The method according to claim 6, wherein the vacuum reduces the pressure initially prevailing in the chamber from 1 bar to below 0.2 bar.

9. The method according to claim 6, wherein the vacuum reduces the pressure initially prevailing in the chamber to below 0.1 bar.

10. The method according to claim 1, wherein the liquid impregnating agent is introduced into the chamber by aspiration through one of the two openings of the chamber by the flow-through of negative pressure.

11. The method according to claim 1, wherein the liquid impregnating agent is introduced into the chamber by pressing it through one of the two openings of the chamber by the flow-through of excess pressure.

12. The method according to claim 1, wherein a pressure in the chamber is cycled more than once.

13. A method for impregnating a porous bone replacement material, comprising:
   introducing a non-curing liquid impregnating agent residing in a first chamber into a second chamber that encloses a porous bone replacement material until the porous bone replacement material is at least partly immersed; and
   reducing a pressure in the chamber to reduce the amount of air in pores of the bone replacement material and to drive the liquid impregnating agent into the pores.

14. The method of claim 13, wherein introducing the liquid impregnating agent includes introducing a liquid containing a body cell.

15. The method of claim 13, wherein introducing the liquid impregnating agent includes introducing a liquid containing a bone marrow component.

16. The method of claim 13, wherein introducing the liquid impregnating agent includes introducing a liquid containing blood.

* * * * *